(12) United States Patent
Guttman et al.

(10) Patent No.: US 6,438,411 B1
(45) Date of Patent: Aug. 20, 2002

(54) DIGITAL ECG DETECTION SYSTEM

(75) Inventors: Michael A. Guttman, Little Falls, NJ (US); Zoran Lazarevic, New York, NY (US)

(73) Assignee: Cardio Technologies, Inc., Pine Brook, NJ (US)

( * ) Notice: Subject to any disclaimer, the term of this patent is extended or adjusted under 35 U.S.C. 154(b) by 0 days.

(21) Appl. No.: 09/358,830

(22) Filed: Jul. 22, 1999

Related U.S. Application Data
(60) Provisional application No. 60/093,918, filed on Jul. 23, 1998.

(51) Int. Cl.[7] .................................................. A61B 5/04
(52) U.S. Cl. ...................................................... 600/521
(58) Field of Search ................................ 600/509, 521, 600/519

(56) References Cited

U.S. PATENT DOCUMENTS

| | | | |
|---|---|---|---|
| 4,240,442 A | 12/1980 | Andresen et al. | ........... 128/704 |
| 5,058,597 A | 10/1991 | Onoda et al. | ............... 126/696 |
| 5,417,221 A * | 5/1995 | Sickler | |

* cited by examiner

Primary Examiner—Scott M. Getzow
(74) Attorney, Agent, or Firm—Darby & Darby

(57) ABSTRACT

An R-wave detection system includes an electrode for placement in close proximity to or in contact with a heart to sense electrical activity of the heart. A signal processor is in communication with the electrode, and is responsive to receipt of the analog signal from the electrode to condition the signal to account for noise and far-field effects. The system is operative to determine whether the conditioned signal exceeds a dynamic threshold value and, if so, the system generates a synchronization pulse to indicate the rising edge of an R-wave.

19 Claims, 3 Drawing Sheets

DIGITAL ECG DETECTION SYSTEM

CROSS-REFERENCE TO RELATED APPLICATIONS

This application claims priority pursuant to 35 U.S.C. § 119, based upon U.S. Provisional Application Serial No. 60/093,918, filed Jul. 23, 1998, the entire disclosure of which is hereby incorporated by reference.

BACKGROUND OF THE INVENTION

1. Field of the Invention

The present invention relates to electrical monitoring systems. More particularly, the invention relates to a monitoring system for monitoring a heart's electrical activity and that triggers upon detecting a rising edge of a R-wave.

2. Discussion of the Related Art

The human heart is a very complicated organ that relies on both mechanical and electrical operation in order to properly perform. As with any complicated mechanism, problems can and do arise, and the heart is no exception. For example, over time the electrical pathways in the heart (which sequentially cause the muscles of the atria and ventricles to contract) may fail, thereby causing the heart to lose its rhythm, which is known as arrhythmia. In such a situation, the heart must be monitored and an external stimulation applied in order to return the heart to normal sinus rhythm. A patient's heart rate must be monitored in many other situations, such as during most surgical procedures, as the patient's heart rate is a good indication of the patient's condition during such a procedure. For that reason, many electronic instruments used in medical procedures employ analysis of a patient's heart rate. The electrocardiogram ("ECG") is one conventional method of determining not only the patient's heart rate, but also for determining potential abnormalities in the patient's heart muscle. As is well known to those of ordinary skill in the art, an ECG is a tracing of the changes of electrical potential that occur within the heart during a heartbeat. In the ECG, the first upward deflection due to contraction of the atria is referred to as a "P-wave", while "Q-waves", "R-waves", "S-waves", and "T-waves" are deflections due to the action of the ventricles.

Recently, automatic detection of the R-waves of the ECG has become important. Detecting R-waves allows for a precise measurement of the patient's heart rate. Automatic detection relieves a surgeon or other trained professional from performing that function. Many of the methods proposed for detecting R-waves are not sufficiently accurate, due to the presence of noise such as power line interference, baseline drift and ECG amplitude modulation with respiration, electrosurgical noise, and the like. In addition, false readings can occur from pacing spikes and T-waves, which are unaccounted for by those proposed methods.

Furthermore, a conventional ECG uses surface-mounted electrodes to monitor the heart's electrical activity, which has shortcomings for detecting rising R-waves. First of all, electrode contact noise often occurs in surface-mounted electrodes, which consists of transient interference caused by the temporary loss of contact between the electrode and the patient's skin. In addition, electrode motion relative to a patient's skin can cause changes in the impedance and consequently changes in the voltage measured. Thus, R-wave detection with surface-mounted electrodes suffers from numerous shortcomings.

Accordingly, it will be apparent that there continues to be a need for an Rwave detection device and method that is designed to account for noise and to avoid false readings from pacing spikes, T-waves, and the like. The present invention addresses these needs and others.

SUMMARY OF THE INVENTION

Briefly, and in general terms, the present invention in one illustrative embodiment is directed to an apparatus for detecting R-waves from a patient's heart. The system is operative to sense the heart's electrical activity, detect the rising edge of an Rwave, and generate a synchronous pulse signal in response thereto. The system is further designed in such a manner that it can continue to function properly during many types of arrhythmias, and does not trigger during T-waves or pacing spikes.

Thus, the present invention in one illustrative embodiment is directed to an apparatus for monitoring electrical activity of a heart and generating corresponding pulse signals upon the monitoring of predetermined conditions, comprising: an electrode that senses electrical activity of the heart; and a signal processor in communication with the electrode to receive electrical activity data from the electrode and determine the magnitude of the electrical activity, the signal processor being programmed to determine whether the magnitude of the electrical activity exceeds an adaptively determined threshold and, if so, to generate a corresponding pulse signal.

The present invention in another illustrative embodiment is directed to a method for determining electrical activity of a heart, including the steps of: detecting a magnitude of electrical activity of at least the ventricles of the heart; setting a threshold value; comparing the magnitude of the detected electrical activity of the ventricles with the threshold value; determining when the magnitude of the detected electrical activity exceeds the threshold value; and generating a corresponding pulse signal.

BRIEF DESCRIPTION OF THE DRAWINGS

The above and still further objects, features and advantages of the present invention will become apparent upon consideration of the following detailed description of specific embodiments thereof, especially when taken in conjunction with the accompanying drawings wherein.

DETAILED DESCRIPTION OF THE PREFERRED EMBODIMENTS

Figure 1:
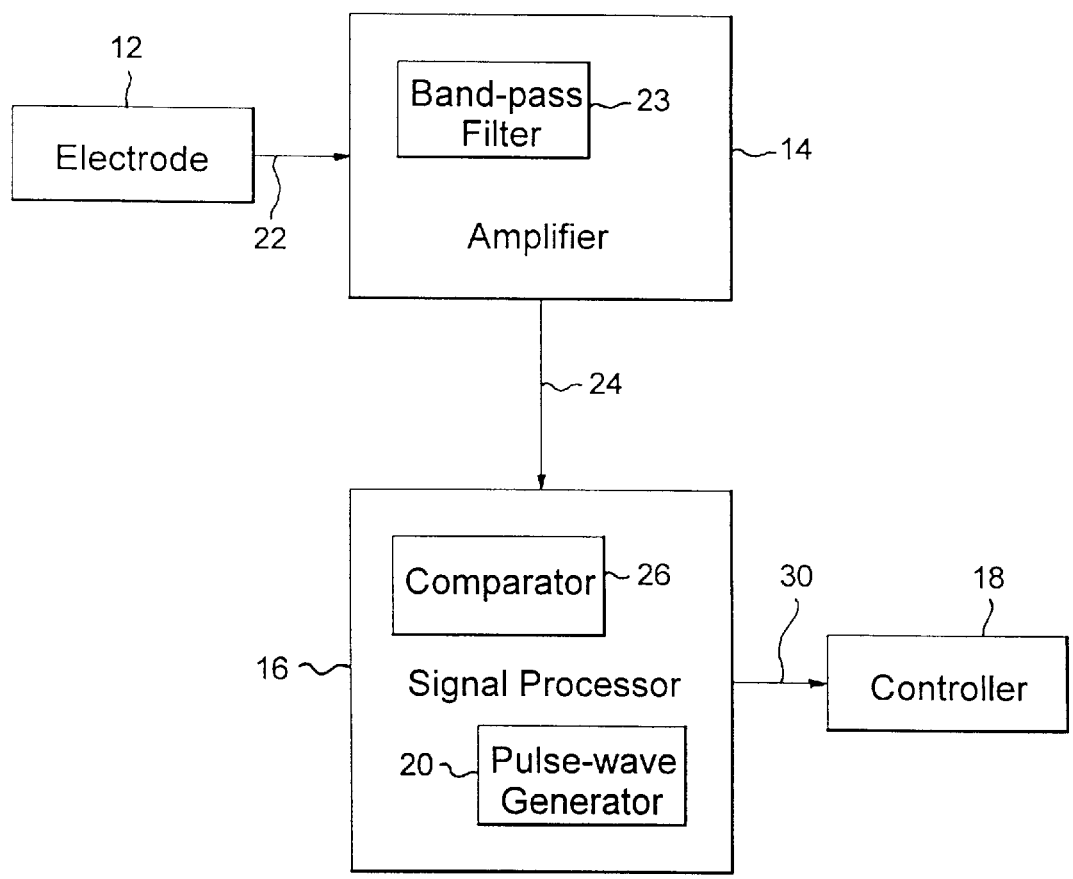
FIG. 1 is a block diagram of an R-wave detection system according to one illustrative embodiment of the present invention.

Referring now to FIG. 1, one illustrative embodiment of an R-wave detection system 10 is shown. The R-wave detection system 10 is preferably operative to sense rising R-waves from a patient's heart, and generate corresponding synchronization pulses for use by other medical devices that utilize analysis of a patient's heart rate. In the illustrative embodiment shown, the system 10 includes an electrode 12, an amplifier 14, and a signal processor 16 including a pulse wave generator 20. The electrode 12 is configured for placement in close proximity to or in contact with a heart to sense electrical activity of the heart. The amplifier is electrically connected to the electrode for communication therewith, and is responsive to receipt of a signal from the electrode to amplify and filter the signal as is described in greater detail below. The signal processor receives the amplified and filtered signal from the amplifier and further conditions the signal to account for noise and far-field effects. The system is then operative to determine whether the conditioned signal passes a dynamic threshold value from a value below to a value above the threshold and, if this occurs while the system is not in a blanking interval, the system generates a synchronization pulse to indicate the detection of a rising edge of an R-wave.

The electrode 12 may take many different forms as is well known to those of ordinary skill in the art. In one illustrative embodiment, the electrode comprises a myocardial electrode configured for placement against or in close proximity to the myocardium of the heart in order to sense the heart's electrical activity in the form of a ventricular electrogram ("VEG"). The electrode is connected to a signal wire 22 leading to the amplifier 14 for one-way communication therewith. In one preferred embodiment, the amplifier comprises an isolation amplifier that receives the incoming analog signal from the electrode and amplifies the signal. The amplifier preferably includes a bandpass filter 23 with a pass band of between about 1 and about 250 Hz. The amplifier also provides patient isolation at the inputs. One suitable amplifier is Model Number IA294 available from Intronics of Newton, Mass.

The filtered, amplified analog signal from the amplifier 14 is output on signal line 24 to the signal processor 16. The signal processor receives the analog signal and is operative to sample the signal at a predetermined frequency. The sampled signal is then filtered, and further conditioned to provide a processed digital VEG signal, as is described in greater detail below in connection with FIGS. 2 and 3. One suitable signal processor includes a SHARC evaluation board and ADSP-2 1061 SHARC floating point signal processing chip, available from Analog Devices.

The signal processor 16 further includes a comparator 26 that serves to compare the magnitude of the processed digital VEG signal with a dynamic threshold value computed by the signal processor. In the event the VEG signal crosses the threshold from below the threshold to above the threshold and the system is not in a blanking interval (which is described in greater detail below), the signal processor controls the pulse wave generator 20 to output a synchronization pulse signal along output line 30. The pulse signal is received by, for example, a controller 18 of an electronic medical instrument connected for one-way communication with the output of the signal processor.

Figure 2:
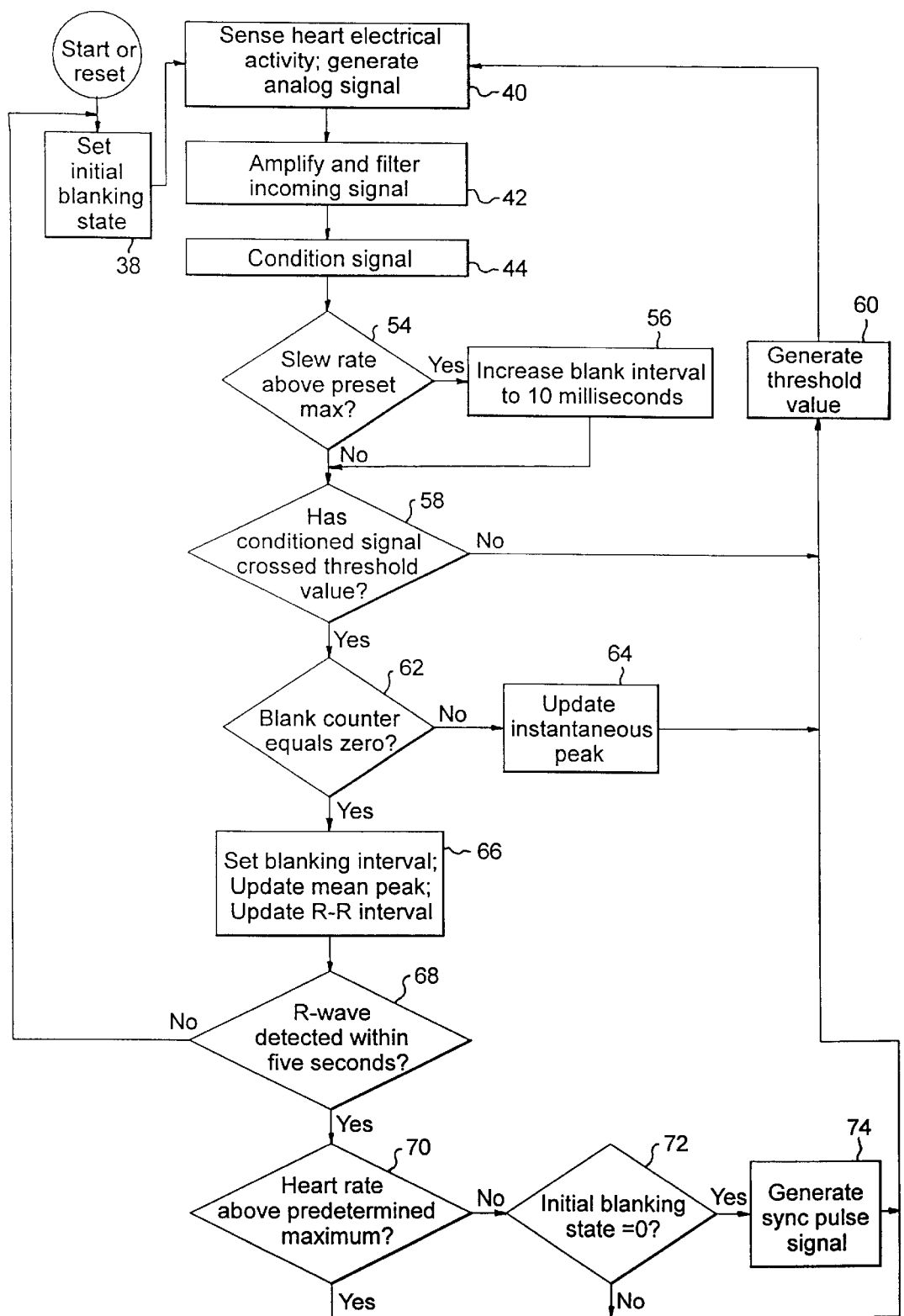
FIG. 2 is a flow chart illustrating the operation of the R-wave detection system of FIG. 1.
Figure 3:
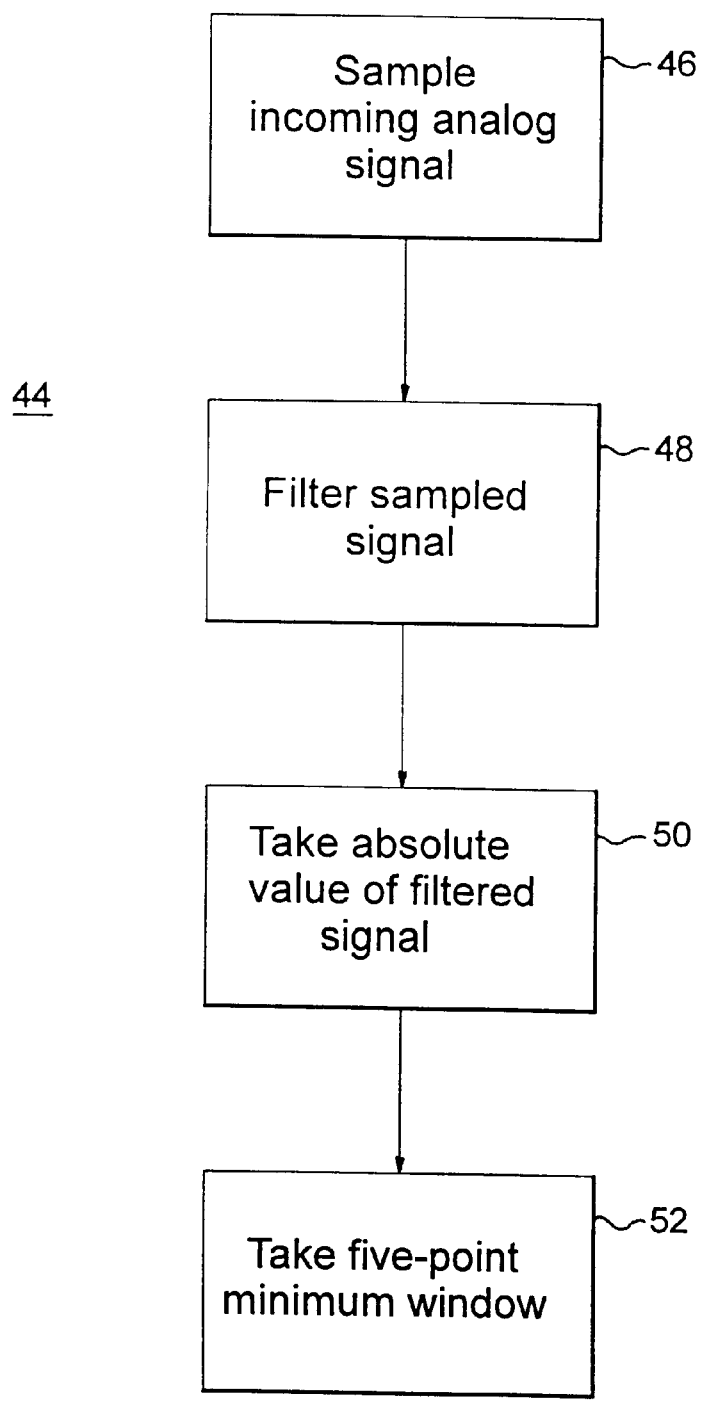
FIG. 3 is a flow chart illustrating additional processes performed by the R-wave detection system of FIG. 1.

Referring now to FIGS. 2 and 3, the operation of the R-wave detection system 10 will be described in greater detail. The electrode is initially manipulated into place in close proximity to or in contact with the heart, for example with the myocardium. The system 10 is then preferably actuated, with the signal processor 16 being programmed to initially enter an initial blanking state at step 38, during which time no synchronization pulses are generated by the system 10, regardless of the electrical activity sensed by the electrode 12. The electrode is operative to sense the heart's electrical activity and generate a corresponding analog signal, at step 40. At step 42, the analog signal is received by the amplifier 14, and is filtered by the bandpass filter 23 and amplified. In one illustrative embodiment, the amplifier has a gain of 50. Next, the filtered and amplified signal is transmitted to the signal processor 16, and the signal is conditioned at step 44.

As shown in FIG. 3, conditioning of the amplified, filtered analog signal by the signal processor 16 involves a number of functions. First, the signal is sampled at a preselected frequency $f_s$, at step 46. In one illustrative embodiment, the sample frequency is 1 kHz. Next, at step 48, the sampled signal is filtered by a simple IIR high-pass filter that is implemented by the signal processor using the following difference equation:

$$y[n]=x[n]-x[n-1]+ay[n-1]$$

where
 $a=1-40/f_s$
 n=the current sample number
 x[n]=the sampled signal.
The frequency response of the IIR high-pass filter has a high pass −3 dB cut-off of between 6 and 7 Hz.

Next, the absolute value of the filtered, sampled signal is taken at step 50, because the polarity of the incoming signal is unknown. Then, at step 52, the signal processor 16 takes a minimum over 5 milliseconds to account for far-field pacing spikes and the like, as well as to provide suppression of spikes from noise. This is a five-point minimum in the illustrative embodiment. In other words, the processor takes five consecutive values, and takes the lowest of the five values. The processed VEG signal z[n] is given by the following equation:

$$z[n]=\min\{|y[n-m]|; m=0,1,2,3,4\}.$$

Next, at step 54 (FIG. 2), the system checks the slew rate of the electrical signal being monitored, which is an additional means for determining whether the electrical activity being detected is a pacing spike rather than the heart's own electrical activity. The slew rate check is given by the following: if $|x[n]-x[n-1]|f_s > S_{max}$, then the pacing blank counter is set to 0.01 $f_s$=10 milliseconds, at step 56. The value $S_{max}$ is a constant set at a preselected maximum allowable slew rate. If the blank count is less than the pacing blank count, then the blank count is set equal to the pacing blank count.

In order to determine whether the threshold is crossed, at step 58 the system 10 checks if the following statements are true:
 1) z[n−1]<t[n−1]; and
 2) z[n]≧t[n].
Thus, where z[n] crosses the threshold from above to below, it will be understood that the system 10 is not triggered, because the first of the two statements is not true. Thus, only when the conditioned VEG signal crosses the threshold value from below to above is the system triggered to generate a synchronization pulse.

If the threshold is not crossed, operation proceeds to step 60, and the signal processor calculates the variable threshold t[n] for comparison with the conditioned VEG signal z[n], at step 54 (FIG. 2). The threshold is an adaptive threshold with a value that exponentially decays toward the value of the processed VEG signal, z[n]. The threshold t[n] is given by the following equation:

$$t[n]=\max\{\alpha z[n]+(1-\alpha)t[n-1], t_{min}\}$$

where
 $\alpha=0$, if pacing blank count>0;
 $\alpha=1$, if z[n]>t[n−1];
 $\alpha=7/f_s$, otherwise.
The use of different time constants results in the threshold t[n] being able to rise quickly and drop slowly to track the VEG signal z[n]. Because the decay time is relatively short when raising the threshold, and relatively long when lowering the threshold, the threshold acts as a peak detector, thereby serving to screen out noise and far field pacing spikes. By setting the time constant to 0 if a pacing spike is detected, the threshold does not respond to potentially large voltage swings during pacing. The minimum threshold value $t_{min}$ is a function of a mean peak sensed, as is described in greater detail below. After the threshold is calculated, operation proceeds back to step 40 for further sensing of the heart's electrical activity by the system 10.

If, however, the threshold is in fact crossed, then the process flows to step 62, where the signal processor 16 checks if a blanking interval counter is equal to zero. The blanking interval counter is equal to zero when the system is not in a blanking state, as is described in greater detail below. If the blanking interval counter is not equal to zero, then the system is in a blanking state and operation flows to step 64 and an instantaneous peak variable $p_z$ is updated with the new value of $z[n]$, after which operation proceeds back to step 40. The instantaneous peak variable $p_z$ records the peak of the conditioned VEG signal $z[n]$ during the blanking period.

If, on the other hand, the blanking interval counter is equal to zero, then the system is not in a blanking state, and operation instead flows to step 66, where the blanking interval counter is reset, such that the system enters a blanking state to prevent additional triggers during the blanking state. The signal processor 16 sets the blanking counter to a predetermined value, for example $0.2f_s$. This effectively sets a blanking interval, during which time no synchronization pulse signals are generated. This prevents the system from false triggering on a T-wave that immediately follows a detected R-wave. It will be apparent that the blanking interval can be set to some value other than $0.2f_s$.

Also at step 66, the mean peak $\rho_z[n]$ is updated in order to smooth beat-to-beat variations. The mean peak is preferably defined by the following IIR filter function:

$$\rho_z[n]=\beta p_z[n]+(1-\beta)\rho_z[n-1],$$

where n is the currently detected R-wave, n−1 is the previously detected R-wave, and $\beta$ is a constant having a value of 0.3.

The mean peak $\rho_z[n]$ is used to calculate the minimum threshold $t_{min}$ according to the following equation:

$$t_{min}=\max\{\rho_z[n]/3,T_{min}\},$$

where $T_{min}$ is a constant set to a preselected value, for example 50 mV.

Further, at step 66, the signal processor is programmed to update a mean R-to-R interval $\tau_r$, which records the average period between detected R-waves. The mean interval $\tau_r$ is a function of the instantaneous R-to-R interval $T_r$, as defined by the following IIR filter equation:

$$\tau_r \beta T_r + (1-\beta)\tau_r,$$

where $\beta=0.3$.

In one illustrative embodiment, $\tau_r$ is initially compared with $T_r$, and if $T_r$ is more than three times $\tau_r$, then $T_r$ is not updated. If, on the other hand, $T_r$ is less than three times $\tau_r$, then $\tau_r$ is updated.

Next, at step 68, the system checks whether an R-wave has been detected within the last five seconds. If not, operation proceeds back to step 38. If an R-wave has been detected in the last five seconds, operation flows to step 70, and the signal processor 16 determines whether the patient's heart rate is below a predetermined maximum heart rate, for example 240 beats per minute. This is determined by checking whether:

$$\tau_r \geq 60f_s/240.$$

If the patient's heart rate exceeds the predetermined maximum heart rate (i.e., $\tau_r<60f_s/240$), then operation flows back to step 40. If not, operation proceeds to step 72, and the signal processor 16 determines whether the system 10 is in the initial blanking state. If so, operation flows back to step 40 and the process continues until the initial blanking state is over.

If it is determined by the signal processor 16 that the patient's heart rate is less than 240 beats per minute and the system is not is the initial blanking state, then operation proceeds to step 74, and the signal processor 16 signals the pulse wave generator 20 to output a synchronization pulse wave along signal line 30 for receipt by, for example, the controller 18. Operation then proceeds back to step 40 and the process is repeated.

The signal processor 16 is further programmed to continually decrement the blanking interval counter, pacing blank interval counter, and the initial blanking interval counter in the event any or all are greater than zero. The initial blanking interval counter is set to a predetermined value, for example two seconds, during which time the system 10 does not generate synchronization pulses, even if the system detects R-waves and the patient's heart rate is less than the predetermined maximum heart rate. In addition, the signal processor maintains an R-wave detection counter that keeps track of the time since the last R-wave was detected. This value is used to set the instantaneous R-R interval $T_r$. Also, if no R-waves are detected in five seconds, the program re-initializes.

The system 10 in one illustrative embodiment further includes a manual reset button (not shown), which may be pressed by an operator to reset the system. Depression of the reset button causes the operation of the signal processor 16 to immediately flow to step 38, where the signal processor enters the initial blanking state such that no synchronization pulse signals are generated by the system 10.

In use, the electrode 12 is moved into position, and the system 10 is actuated. The signal processor 16 enters an initial blanking state for a preselected period of time, for example two seconds. During that period, the electrode senses electrical activity of the heart, the amplifier 14 amplifies and filters the incoming signal, and the processor conditions the signal and compares the conditioned signal to the variable threshold. However, even if the conditioned signal passes the threshold from a value below to a value above the threshold, no synchronization pulse is generated by the signal processor.

Once the initial blanking state is over, if the conditioned signal passes the threshold from a value below to a value above the threshold, a synchronization pulse is generated by the pulse wave generator 20. The signal processor 16 then enters a blanking interval to prevent false triggering on the T-wave that follows the R-wave. The blanking interval is sufficiently short such that the interval ends well before the next R-wave is generated by the patient's heart.

From the foregoing, it will be apparent that the present invention provides a reliable, efficient system for automatically detecting R-waves and for generating corresponding synchronization pulses. In addition, the system conditions the incoming electrical signal to account for noise and far-field spikes, and prevents false triggering on T-waves and other sensed voltage peaks.

While the invention has been particularly shown and described with reference to illustrative embodiments thereof, it will be understood by those skilled in the art that various changes in form and details may be made therein without departing from the spirit and scope of the invention. Accordingly, it is not intended that the invention be limited, except as by the appended claims.

What is claimed is:

1. A method for detecting electrical activity of a heart and for generating corresponding pulse signals in predetermined situations, the method including the steps of:

detecting a magnitude of electrical activity of at least the ventricles of the heart;

calculating a variable threshold value;

comparing the magnitude of the detected electrical activity with the threshold value;

determining when the magnitude of the detected electrical activity passes from a value below the threshold value to a value above the threshold value; and if the magnitude of the detected electrical activity passes from a value below the threshold value to a value above the threshold value, generating a pulse signal;

determining whether a slew rate of the sensed electrical activity exceeds a preselected threshold and, if so, preventing the generation of the pulse signal for a predetermined period of time.

2. The method of claim 1, wherein the step of calculating a variable threshold value includes selecting a minimum value constraint for the threshold value.

3. The method of claim 1, wherein the variable threshold is the magnitude of a function of the detected electrical activity.

4. The method of claim 1, wherein the step of detecting includes generating an analog signal of the electrical activity of the heart.

5. The method of claim 4, wherein the step of comparing includes sampling the analog signal at a preselected frequency.

6. The method of claim 5, wherein the step of comparing includes sampling the analog signal at a frequency of about 1000 Hz.

7. The method of claim 1, wherein the step of comparing includes taking the absolute value of the detected signal.

8. The method of claim 1 further including the step of determining whether the heart rate is above a preselected maximum rate and, if so, at least temporarily preventing the generation of pulse signals.

9. The method of claim 1, wherein the step of comparing includes taking a minimum value from at least three consecutive values of the detected electrical signal, and comparing the minimum value with the variable threshold.

10. The method of claim 1 further including the step of:

after generating the pulse signal, entering a blanking state of predetermined duration to prevent the generation of additional pulse signals during the blanking state.

11. A system for monitoring electrical activity of a heart and generating corresponding pulse signals in predetermined situations, the system comprising:

a heart sensor configured to be placed in close proximity to the heart and that senses electrical activity of the heart and generates corresponding electrical signals; and a signal processor in communication with the heart sensor to receive the electrical signals, the signal processor being programmed to condition the electrical signals, to calculate a variable threshold value, and to determine whether the magnitude of the conditioned electrical signal passes from a value below the threshold value to a value above the threshold value and, if so, to generate a corresponding pulse signal; wherein the processor is programmed to determine whether a slew rate of the sensed electrical activity exceeds a preselected threshold and, if so, prevent the generation of the pulse signal for a predetermined period of time.

12. The system of claim 11, wherein the heart sensor comprises an electrode.

13. The system of claim 12, wherein the electrode comprises a myocardial electrode.

14. The system of claim 11, wherein the variable threshold set by the processor is at least equal to a preselected minimum value.

15. The system of claim 14, wherein the variable threshold is the magnitude of a function of the electrical signal received from the sensor.

16. The system of claim 11, wherein the sensor is operative to generate an analog signal of the electrical activity of the heart; and the signal processor is operative to sample the analog signal at a predetermined frequency.

17. The system of claim 16, wherein the signal processor is operative to take the absolute value of the sampled signal.

18. The system of claim 11, wherein the processor is programmed to determine whether a sensed heart rate is above a preselected threshold and, if so, at least temporarily prevent the generation of pulse signals.

19. The system of claim 11, wherein the processor is programmed to take a minimum value from at least three consecutive values of the detected electrical signal, and to compare the minimum value with the variable threshold.

* * * * *